United States Patent [19]
Smith et al.

[11] Patent Number: 5,423,964
[45] Date of Patent: Jun. 13, 1995

[54] COMBINED ELECTROPHORESIS-ELECTROSPRAY INTERFACE AND METHOD

[75] Inventors: Richard D. Smith; Harold R. Udseth; Charles J. Barinaga, all of Richland, Wash.

[73] Assignee: Battelle Memorial Institute, Richland, Wash.

[21] Appl. No.: 100,882

[22] Filed: Aug. 2, 1993

[51] Int. Cl.$^6$ .................. G01N 27/26; G01N 27/447; H01J 49/04
[52] U.S. Cl. ........................... 204/180.1; 204/299 R; 250/288
[58] Field of Search ................ 204/299 R, 180.1; 250/288

[56] References Cited

U.S. PATENT DOCUMENTS

| | | | |
|---|---|---|---|
| 4,842,701 | 6/1989 | Smith et al. | 204/180.1 |
| 4,885,076 | 12/1989 | Smith et al. | 204/299 R |
| 4,994,165 | 2/1991 | Lee et al. | 250/288 X |
| 5,115,131 | 5/1992 | Jorgenson et al. | 250/288 |

OTHER PUBLICATIONS

Richard D. Smith, Charles J. Barinaga, and Harold R. Udseth, "Improved Electrospray Ionization Interface for Capillary Zone Electrophoresis-Mass Spectrometry" Analytical Chemistry vol. 60 No. 18, (Sep. 1988) 1948–1952.
Richard D. Smith, Harold R. Udseth, Charles J. Barinaga, Charles G. Edmonds "Instrumentation for high-performance capillary electrophoresis-mass spectrometry" Journal of Chromatography, 559 (1991) 197–208.
"Attomole Level Capillary Electrophoresis-Mass Spectrometric Protein Analysis Using 5 µm i.d. Capillaries", J. H. Wahl, D. R. Goodlett, H. R. Udseth, R. D. Smith, Anal. Chem., 64, 3194–3196 (Dec. 1992).
"Use of Small-Diameter Capillaries for Increasing Peptide and Protein Detection Sensitivity in Capillary Electrophoresis-Mass Spectrometry," J. H. Wahl, D. R. Goodlett, H. R. Udseth, R. D. Smith, Electrophoresis, 14, 448–457 (1993).
"Capillary Electrophoresis-Mass Spectrometry," R. D. Smith, J. H. Wahl, D. R. Goodlett, and S. A. Hofstadler, Anal. Chem., 65, 574A–584A (Jul. 1993).
"Sheathless Capillary Electrophoresis-Electrospray Ionization/Mass Spectrometry using 10 µm i.d. Capillaries: Analysis of Tryptic Digests of Cytochrome c," J. H. Wahl, D. C. Gale, and R. D. Smith, J. Chromatography.

Primary Examiner—John Niebling
Assistant Examiner—John S. Starsiak, Jr.
Attorney, Agent, or Firm—Johnnie R. Hynson

[57] ABSTRACT

An improvement to the system and method for analyzing molecular constituents of a composition sample that comprises improvements to an electrospray ionization source for interfacing to mass spectrometers and other detection devices. The improvement consists of establishing a unique electrical circuit pattern and nozzle configuration, a metallic coated and conical shaped capillary outlet, coupled with sizing of the capillary to obtain maximum sensitivity.

6 Claims, 8 Drawing Sheets

COMBINED ELECTROPHORESIS-ELECTROSPRAY INTERFACE AND METHOD

This invention was made with Government support under Contract DE-AC06-76RLO 1830, awarded by the U.S. Department of Energy. The Government has certain rights in the invention.

FIELD OF THE INVENTION

The present invention relates generally to a system and method for analyzing molecular constituents of a liquid sample wherein the liquid solution is separated into an eluent by capillary zone electrophoresis (CZE), or other small-scale separation methods, followed by electrospraying the eluent for detecting the ionized molecular components. More specifically, the invention relates to how high voltage is applied to the liquid sample.

INCORPORATION BY REFERENCE

This application incorporates by reference U.S. Pat. No. 4,885,076 to Smith, Udseth, and Olivares, and is an improvement and technical extension thereon.

BACKGROUND OF THE INVENTION

The present invention relates to a method. and apparatus for analyzing chemical compositions; more particularly, in electrode and design interface configuration. It is relevant to separations using capillary electrophoresis, but it is also applicable to analysis of any liquid delivered through a small diameter capillary.

Prior Art CZE System

FIG. 1 is a schematic illustration of the arrangement of a CZE system prior to the '076 patent. In this apparatus, a complete high voltage electrical circuit must be formed between opposite ends of a fused silica capillary A. This capillary is filled with buffer solution J and extends through a fluorescence detector B containing an optical window G where the analysis is accomplished. The electrical circuit begins when a high voltage source E is applied to the buffered solution in beaker C and uses the buffered solution J within the fused silica capillary A as a path of conductance to the ground potential F applied to the buffered solution J in beaker D.

CZE detection as illustrated in FIG. 1 is currently limited to analysis by ultraviolet (UV) or fluorescent detection techniques. In addition, CZE detection by the system of FIG. 1 is limited to a narrow range of solutions that can be used and soluents. These limitations were overcome by the apparatus disclosed in U.S. Pat. No. 4,885,076 to Smith, Udseth, and Olivares ('076).

Summary of the Method of the '076 Patent

FIG. 2 illustrates the method of the use of the CZE system as disclosed by the '076 patent. In this method a sample solution 1 contained in beaker 2 is analyzed by mixing it with a buffered solution 3 from beaker 4, and then applying the potential from a first high voltage source 5 via the first high voltage electrode 6 to the buffered solution 3. This potential will also be applied to the buffered solution 3 sample solution mixture 1 that is within capillary 7. Potential from a second high voltage source 8 will be applied to a metallic nozzle 9 via the second high voltage electrode 10. These potentials will cause the constituents with the buffered solution 3 and sample solution 1 mixture to be temporarily distributed along the capillary 7. The end result being a cone-shaped electrospray 12 of the mixture at the ESI tip 13 into the analytical detection device 14, which is connected to a common ground with the CZE circuit via detector lead 16 and the second node 18. The first high voltage source 5 is connected to the common ground via ground lead 20 at the first node 22.

Improvements in the Background by the '076 Patent

The '076 patent discloses a system and method for interfacing the free zone electrophoretic separation of a sample and eluent, respectively, so that the molecular constituents of the electrosprayed eluent can be analyzed.

FIG. 2 is a schematic representation of the apparatus disclosed by the '076 patent.

This invention, though of greater utility that the earlier CZE apparatus of FIG. 1, still had limitations. Specifically, high sample flow rates was needed requiring a large diameter capillary and corresponding current. A portion of the capillary electric current was lost and did not reach the mass spectrometer (MS), or other detection unit, and the capillary solution flow and electrical current were unstable in certain situations. Additionally, despite the advances of the apparatus disclosed in the '076 patent suffered from background noise that further reduced sensitivity.

SUMMARY OF THE INVENTION

The instant invention is an improvement on the device disclosed in U.S. Pat. No. 4,885,076, which is incorporated by reference.

The improvement consists of connecting a high voltage source to an improved capillary tip design at the CZE-MS interface, an insulating nozzle containing a multiplicity of sheaths for solution flow, and an electrode connection remote from the nozzle. This achieves a higher degree of sensitivity and stability than placing the electrical potential at the interface, and allows for the use of a broader range of the types of solutions.

The insulating nozzle and the remote electrode connection of the instant invention allow for greater stability for the critical ESI source voltage. This is accomplished by a "feedback" feature inherent in the preferred embodiment of the instant invention, increasing the stability of the capillary current, and increasing the sensitivity of the CZE-MS apparatus.

The ESI source voltage is determined by the voltages at the remote ends of the two capillaries and their effective resistances. One aspect of the instant invention is a configuration enabling the ESI apparatus to dampen the transient felt at the ESI tip when a transient in resistance occurs in one capillary. This transient affects the voltage which tends to re-establish the optimum voltage at the ESI tip.

Another element of the instant invention is the shaping of the capillary tip into a conical shape. This improved tip design has been found to improve the electrospray stability by producing a smaller outside diameter capillary at the point of electrospray formation, which yields a higher electric field. Even greater stability is found when the conical shaped portion of the tip has a metallic coating.

The instant invention can be designed to provide up to approximately two orders of magnitude smaller flow that the '076 patent and permits the use of aqueous solutions and buffers in addition to organic liquids. This has an added advantage in that it solves the problem of the organic solvents degrading the gel used in polyacrylamide gel or polymer solution-filled capillaries.

The use of the smaller capillaries is advantageous in that it enables the use of smaller electrical currents, that in turn cause less of the limited sample size to be consumed. This produces extremely stable ESI currents by providing a sheath flow that delivers electrolyte to the ESI source (tip) at approximately the rate optimum to sustain the ESI current. A further advantage is a reduction in background noise by a factor of 100 as compared to the '076 patent.

A preferred mode of application of the instant invention is the use of sulfur hexafluoride ($SF_6$), as an outer sheath gas to scavenge electrons and to prevent the formation of corona discharge. A further increase in stability is achieved when the $SF_6$ is used with an etched fused silica capillary tip that has been etched with hydrofluoric acid to a roughly conical tip. This allows liquids such as water to be electrosprayed successfully and allows for sufficient stability when the ion signal with 100 ms averages less than 5% variation. This increase in stability is due to the higher electric field at the ESI tip, which is due to the use of the small o.d. inner capillary, and is facilitated by the etched conical tip.

A sheath is a cylindrical annulus carrying a flow to the capillary tip. Often, a plurality of sheaths are used for transporting selected liquids and gases to the capillary tip.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
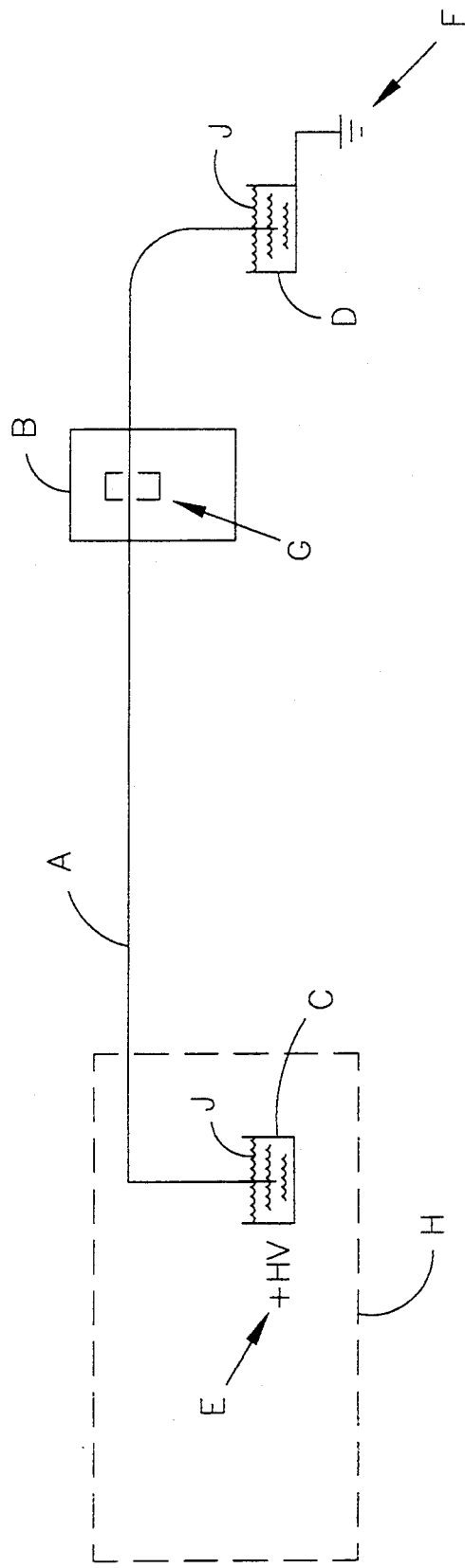
FIG. 1 is a schematic illustration of a conventional apparatus used for capillary zone electrophoresis.
Figure 2:
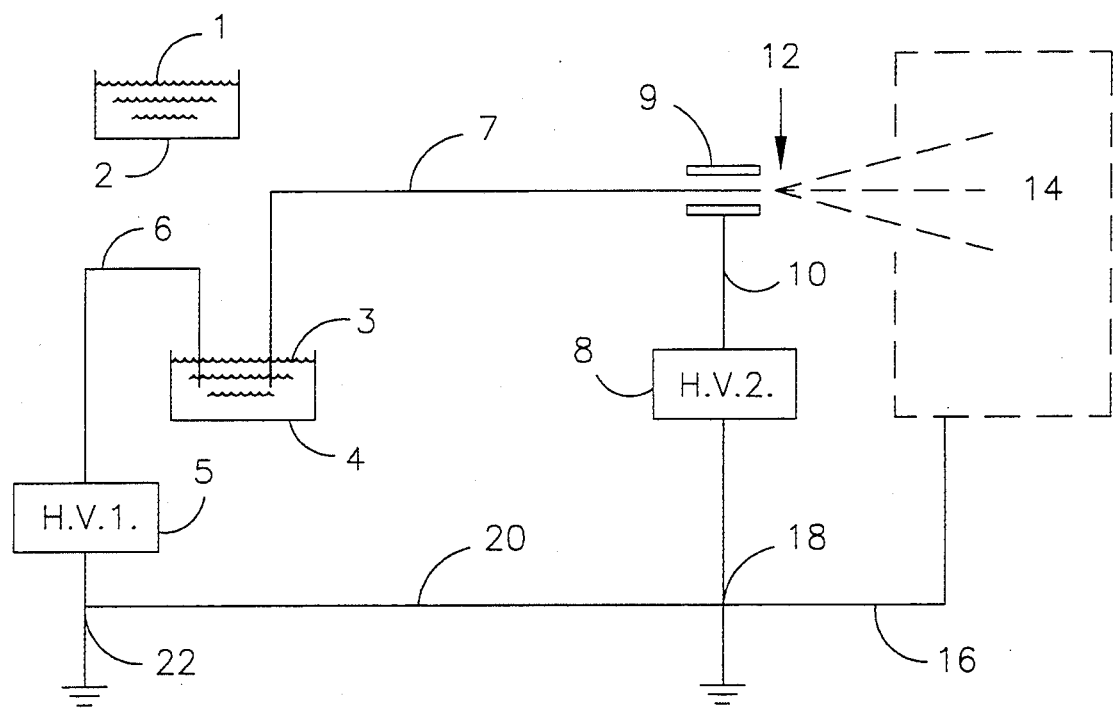
FIG. 2 is a schematic illustration of the apparatus used for capillary zone electrophoresis in the '076 patent.

The instant invention is an improvement of the apparatus of the '076 patent as illustrated in FIG. 2, which is an advancement over the customary method of doing capillary electrophoresis as illustrated in FIG. 1.

Improvements Over The '076 Patent

Figure 3:
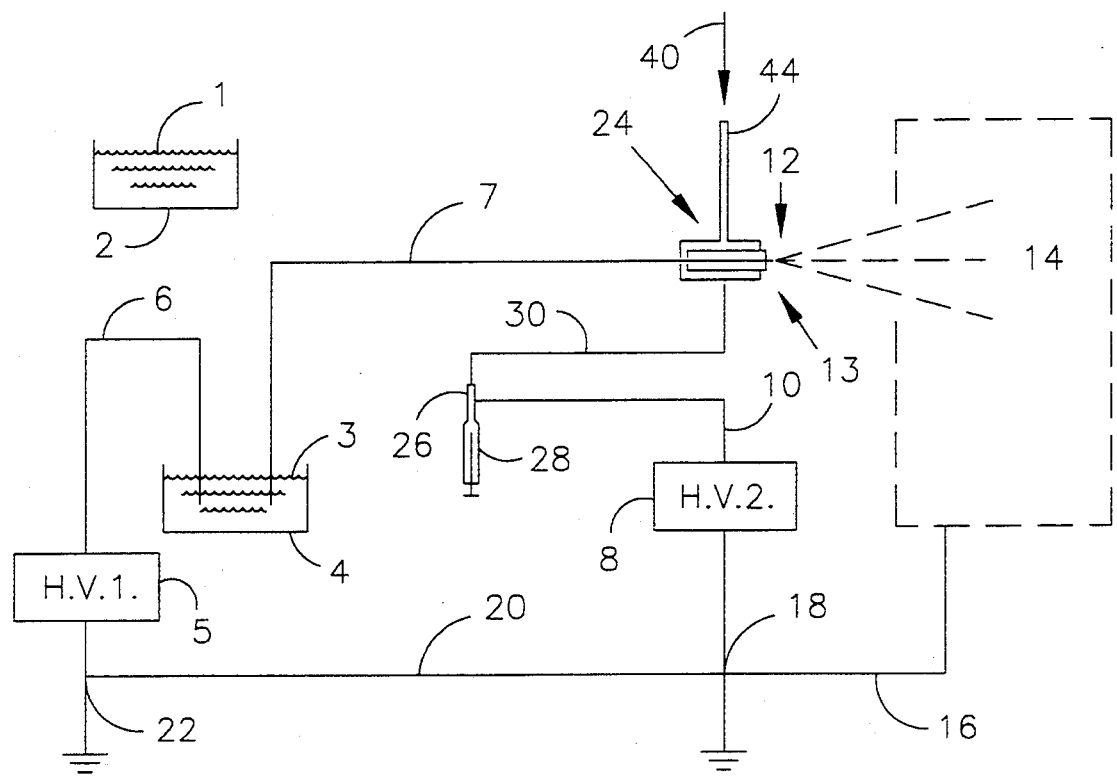
FIG. 3 is an electrical circuit diagram of the apparatus or CZE-MS in accordance with the instant invention.

As illustrated in FIG. 3, the improvements are the change in placement of the second high voltage electrode 8 from the metallic nozzle of FIG. 2 to that of the syringe needle 26 of FIG. 3, which is part of the syringe pump 28, and the replacement of the metallic nozzle 9 of FIG. 2, with the insulated nozzle 24 of FIG. 3.

Figure 4:
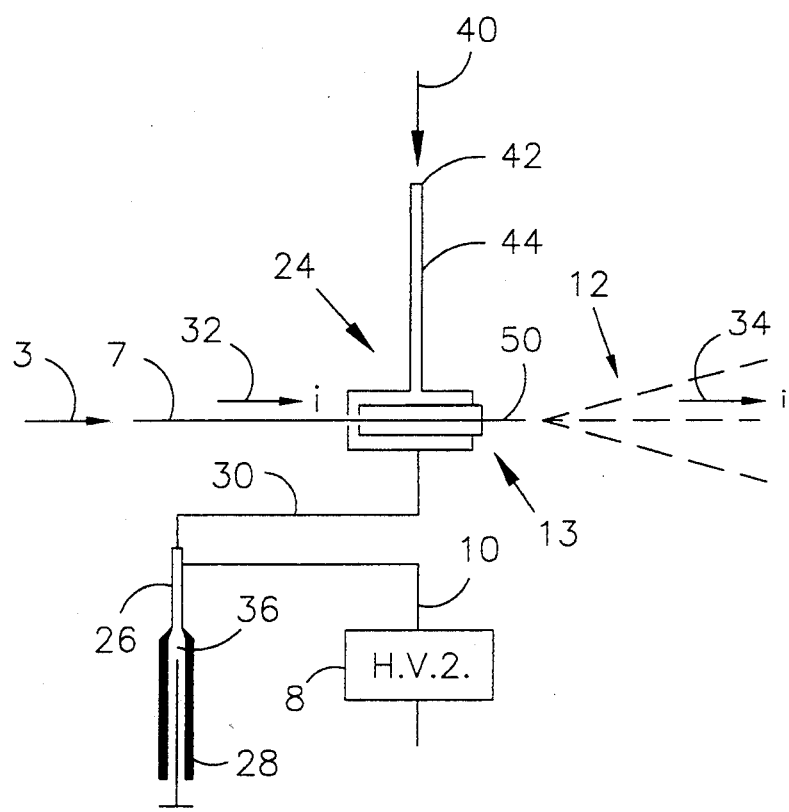
FIG. 4 is an enlarged portion of FIG. 3 illustrating the location of the improvements over the '076 patent.

Referring now to FIG. 4, these changes allow for adjustment of the flow of the buffered solution 3 from beaker 4 and improves the ability to achieve a balance between the capillary current 32 and the electrospray current 34. A second capillary 30 connects the syringe needle 26 to the insulated nozzle 24 that carries a sheath liquid 36. Buffered solution 3 and sheath liquid 36 are the same liquid and are typically, but not restricted to, buffered solutions, such as acetic acid.

The capillary current 32 is the total current that flows from the first high voltage source 5 within the buffered solution 3 that flows within the capillary 7. The electrospray current 34 is that portion of the capillary current 32 that passes into the detector 14 from the ESI tip 13.

In FIGS. 2 and 3 electrical lead 6 applies the voltage to the buffered solution 3 in beaker 4. Also, the electrical leads 16 and 20 connect the high voltage sources 5 and 8 to ground potential through node 18.

Electrical Connection of H.V. 2 to the ESI Spray

The second capillary 30 is electrically isolated from the nozzle 24 by the selection of proper insulating materials for construction of the capillary wall 31. By connection of the second high voltage lead 10 to the needle 26 the electrical potential of second high voltage sources 8 is transmitted to the sheath liquid 36 by virtue of its direct contact with the needle 26. The second high voltage source 8 is then felt at the spray 12 due the sheath liquid 36 conducting the charge to the sheath liquid 36 that is at the inner sheath 38. However, due to the insulating nature of the capillary wall 31 construction the second high voltage potential 8 is isolated form the nozzle 24 itself.

Use of Syringe Pumps

Shown in FIG. 3 is a syringe pump 28 used to pump buffered solution 3 down the capillary into the inner sheath 38. The buffered solution 3 injected by the syringe pump is the same buffered solution 3 in the beaker 4.

Figure 5:
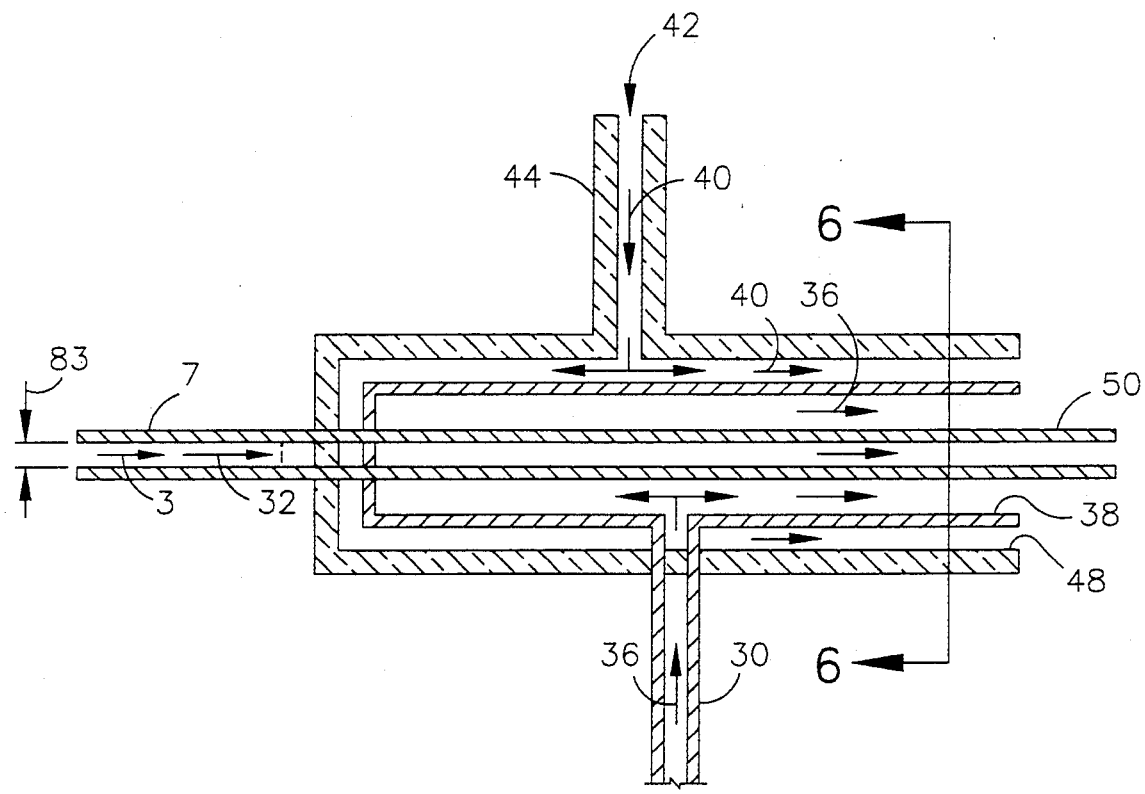
FIG. 5 is a cross section of the insulating nozzle used in accordance with the instant invention.

Shown in FIG. 5, the inner sheath 38 is connected to the syringe pump 28 via the syringe needle 26 and a second capillary tube 30. In the instant invention the syringe needle 26 of the syringe pump 28 is connected to the second high voltage lead 10. Sheath and annulus are used synonymously in this application.

Since the buffered solution that flows from the syringe pump 28 is in direct contact with the output from the second high voltage source 24, that potential is applied to the sheath liquid 36 (which is the same as the buffered solution 3) that flows out of inner sheath 38.

The voltage is therefore applied at the exit of the inner sheath 38.

Use of Other Pumps

While a syringe pump is shown and described it will be apparent to those skilled in the art that the invention is not so limited. Any low-volume-controlled-flow pump that permits electrical contact with the pumped sheath liquid 36 can be used with the instant invention.

Lower Flow Rates Reduces Background Signals

The use of low volumetric flow rate pumps are necessary in that they give the added advantage of the reduced sheath flow rates, greatly reducing the background signals due to impurities in the sheath liquids. These impurities can cluster with the solvent molecules and can span a large portion of the mass spectrum that until now has limited the ultimate sensitivity of the CZE-MS apparatus.

Remote Location of the Electrodes

This remote location of the second high voltage electrode 10 is advantageous in that it allows for easier adjustment of the balance between the capillary current 32 and the electrospray current 34.

Description of Insulated Nozzle

Figure 6:
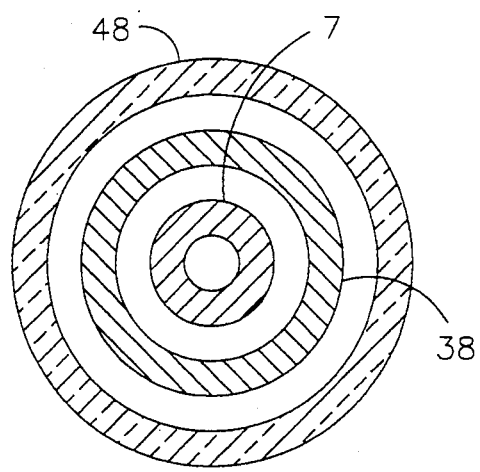
FIG. 6 is a cross section along lines 6—6 of the insulating nozzle used in accordance with the instant invention.

FIGS. 5 and 6 illustrate the configuration of the insulated nozzle 24 used in the instant invention. Since the control of capillary current 32 is important to this invention, the insulated nozzle 24 and capillaries 7, 30 should be constructed out of insulating material such as vinyl or fused silica. The insulated nozzle 24 consists of a series of annuli or sheaths that directs the combined, and adjoining, flows of the buffered solution 3 and the sample solution 1 to the ESI tip 13 of the insulated nozzle 24 where it is shaped into a cone-shaped mist 12 directed toward the detector 14. The second capillary 30 from the syringe pump 28 directs buffered solution 3 to the inner sheath 38.

$SF_6$ 40 is introduced into the apparatus at an entry point 42 into a tube 44, that carries $SF_6$ 40 to the insulated nozzle 24, which directs the $SF_6$ 40 to the outer annulus 48, which directs the flow to the ESI tip 13, where it is mixed with flow from inner sheath 38 and ejected from the capillary outlet tip 50. The $SF_6$ 40 is used as an electron scavenger and to enable the use of a broader range of eluents. The use of $SF_6$ 40 is not critical to the use the instant invention; however, the test results discussed below were obtained using $SF_6$ 40, and it is common practice within the art to use $SF_6$ 40. The $SF_6$ 40 scavenges the excess electrons and suppresses electrical discharges which will often occur at a lower voltage than the onset of ESI. Oxygen may be used, as well as other electron scavenging gases, but $SF_6$ 40 is preferred because of better combustion and dielectric properties.

Applicants have determined that optimum results are obtained with capillaries of relatively small diameters. A typical diameter for the capillary 7 will be between about 10 to 20 $\mu m$. The results of the test discussed below were obtained using a capillary size of 20 $\mu m$. The difference between radii of the inner sheath 38 and the annulus 48 should be from 10 to 40 $\mu m$. The length of the insulated nozzle 24 is not critical to the instant invention.

Nozzle geometry was also found to influence sensitivity. When the capillary 7 protrudes up to a millimeter beyond the other annuluses in the direction of the MS unit, optimum results were obtained. The use of a metallic coating 54 on the tip of the capillary 7 can facilitate a larger distance of protrusion of the capillary outlet tip 50 from the inner sheath 38. This is because the metallic coating 54 improves the electrical connection between buffered solution 3 and the sheath liquid 36 that was weakened when the distance separating them was increased by the protrusion of the tip.

All flows from all annuluses are directed toward the detector 14 where they will be analyzed. The flow 12 from the insulated nozzle 24 takes the form of a cone. The electrical contact of all of the flows allows for a unique ability to control capillary current 32 and for additional current stability.

Conical Shape of the Capillary Outlet

Figure 7:
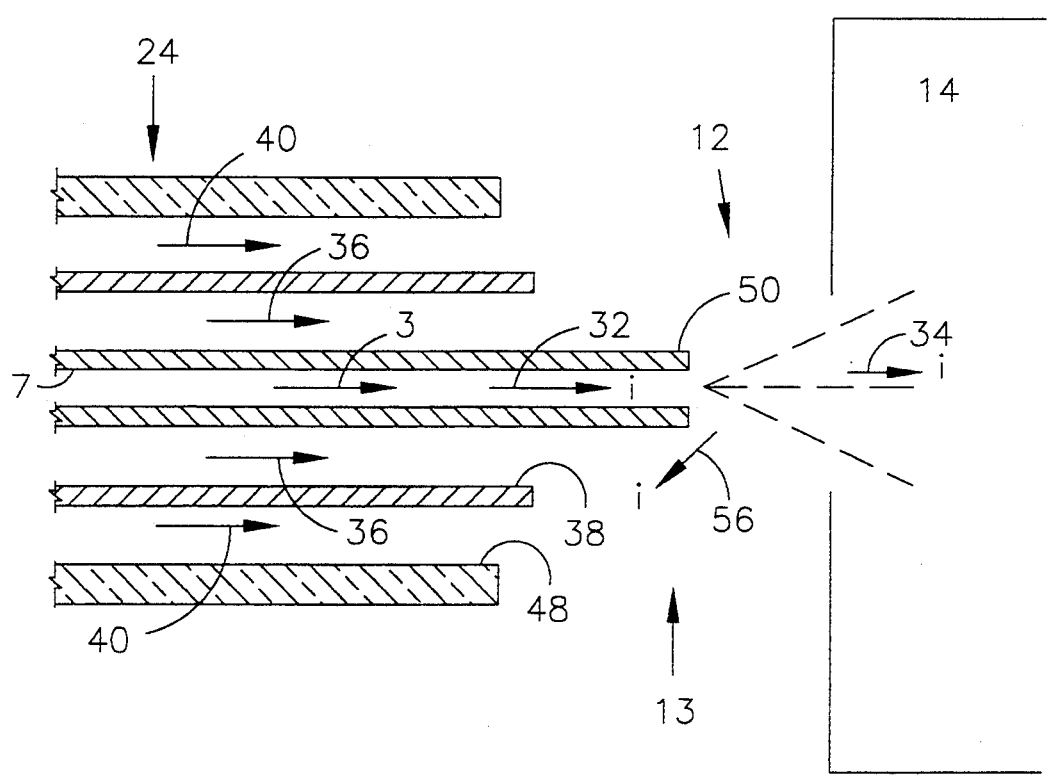
FIG. 7 is an enlarged portion of FIG. 5 illustrating the ESI tip.
Figure 7A:
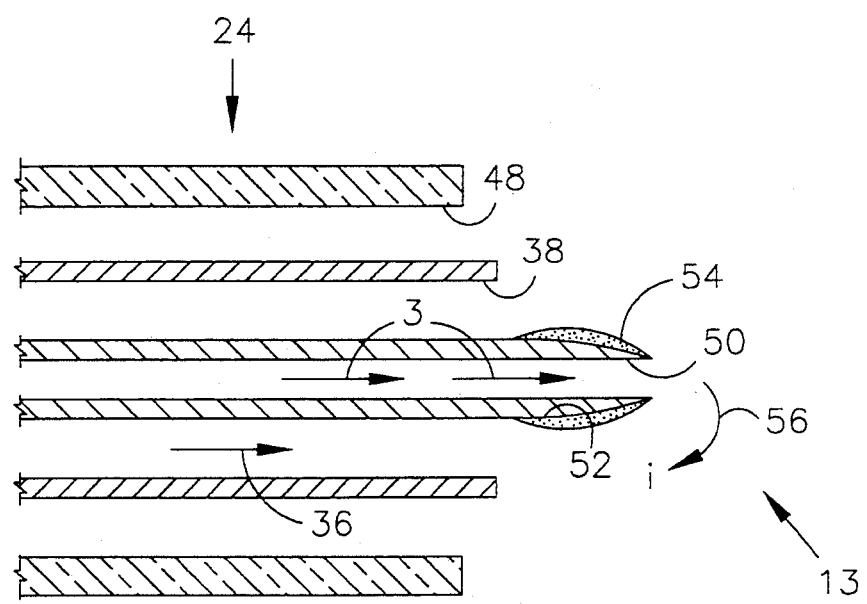
FIG. 7a is an enlarged portion of FIG. 5 illustrating the use of the metallic coating and the conical shaped tip.

Referring to FIG. 7a, the use of an etched fused silica capillary offers an added advantage when the outer surface of the capillary outlet tip 50 has been etched with hydrofluoric acid to a roughly conical shape 52. This shape permits the sheath liquid 36, consisting of fluids such as water, to be electrosprayed successfully, and further improves stability which is when the ion signal is at or below 100 ms averages with less than 5% variation.

Metallic Coating of the Capillary Outlet

The use of metallic coating 54 on the capillary outlet tip 50 increases flow and electrical stability, as illustrated in FIG. 7a. The metallic coating 54 improves the conduction of potential and current flow 56 between the two sheath liquids 36, 44. Additionally, the metallic coating increases the electrical field for a given voltage felt at the ESI tip 13.

Current Feedback Feature

The path of current in the prior art applications and in the '076 patent is from the first high voltage source 5 through the buffered solution 3 within the capillary 7 and to a metallic nozzle 9, and thence to the second high voltage source 24. This has the effect of separating the circuit of the electrophoresis portion of the apparatus from that of the electrospray. This method typically caused a large difference between the capillary current 32 and the electrospray current 34. In the '076 patent, capillary current 32 on the order of approximately 10 $\mu A$ can typically be expected in the capillary 7, while a current in the order of approximately 0.2 $\mu A$ can be expected from a typical electrospray emitter.

As illustrated in FIG. 7, the capillary current flow in the instant invention is directed along the capillary 7 to the ESI tip 13, and thence into the detector 14 under properly balanced conditions. The proper balance is achieved by adjusting the voltage of the second high voltage source 24 such that the electrospray current 34 is stable. The flow of the buffered solution 3 is also a useful variable for adjusting the electrospray stability. The exact current path from the capillary 7 to the detector 14 is not known, nor is the differential current path 56 from the buffered solution to the sheath fluid 36 exactly known. But if the these currents within the system is not balanced, the difference in capillary current 82 and the electrospray current 34 (the differential current path 56) is supplied by the second high voltage source 24. This in effect links the detector 14 and the electrophoresis unit Changes in the capillary current 32 are dampened by the configuration of the system in a self-stabilizing manner.

The ESI tip 13 voltage is effectively determined by a voltage divider, with the resistances of the capillary 7 and the resistance of the second capillary tube 30 being the resistance legs of the voltage divider. The potential felt at the outlet end of each capillary is determined by the high voltage power supplies at the other ends of the respective capillaries.

Changes in the electrical connection between the two high voltage power supplies 18,24 are felt at the capillary tip and may vary due to the stability of the sheath flows 36,40 and the buffering solution 3. This is particularly seen when the capillary outlet tip 50 protrudes outwardly from the inner sheath 38 and annulus 48. These flow instabilities cause an increase in the effective resistance in the electrical circuit that is driving the ESI flow. An increase in resistance of this leg will cause the voltage at the capillary outlet tip 50 to increase, which will tend to reestablish the electrospray and the electrical contact between the two high voltage power supplies 5,8. Thus, the circuit has a feedback mechanism that tends to be self-correcting. When the capillary current 32 drops in value, this in effect increases the effective resistance of that leg of the voltage divider, thereby reestablishing the capillary current 32, which stabilizes the operation of the CZE.

Capillary Size Influences Capillary Current

Figure 8:
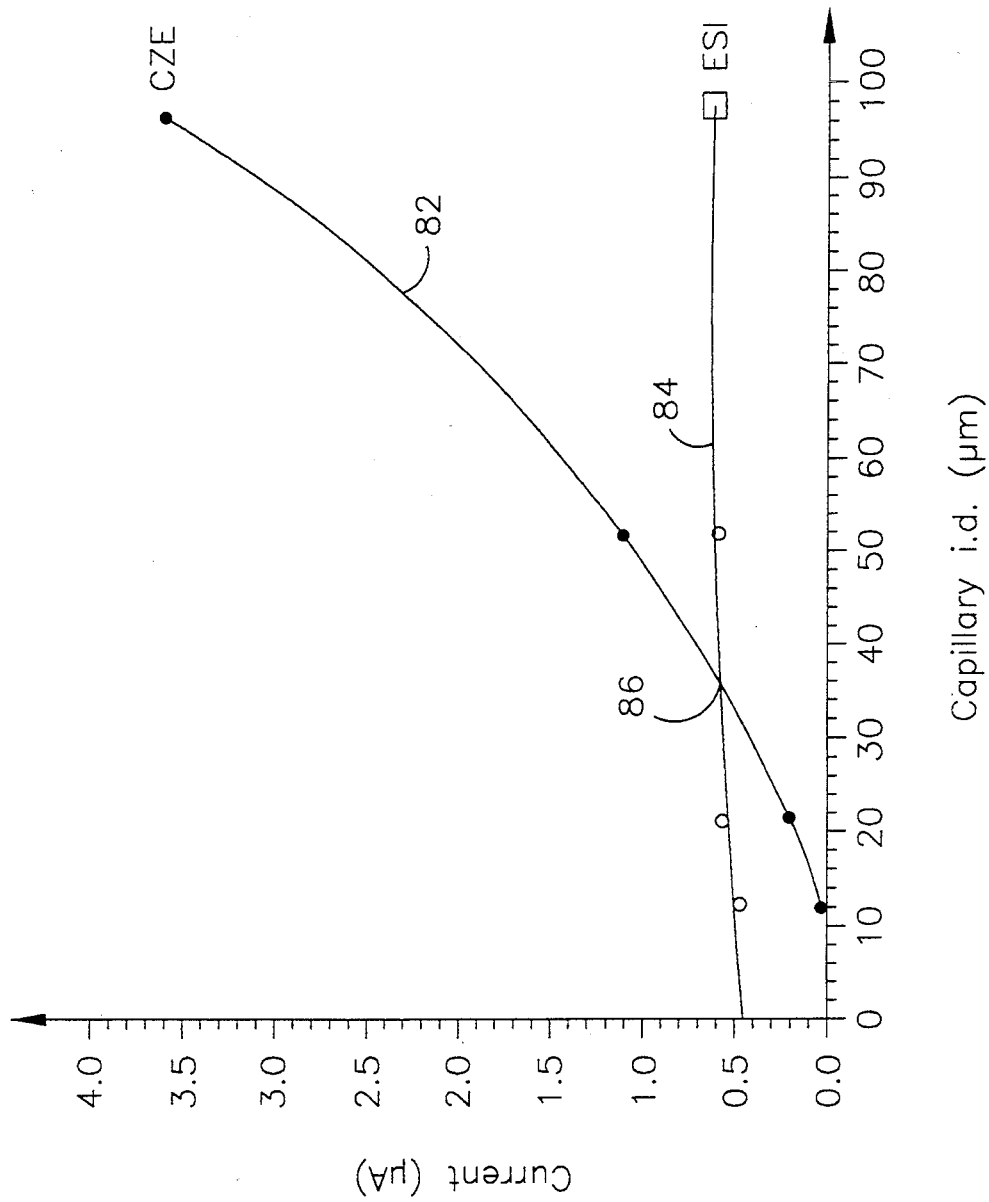
FIG. 8 is a graphical representation of capillary current versus/the capillary inside diameter (i.d.) for ESI and CZE.

The size of the capillary 7 in the CZE application of the instant invention is proportional to the capillary current 32. As mentioned previously, capillary 7 size is an important aspect of the instant invention. The curve 82 in FIG. 8 illustrates this relationship, which is a plot of capillary current 32 versus the capillary i.d. 83 in the CZE configuration. The curve 84 in FIG. 8 also illustrates the relationship of the current that makes it into the detector 14 in the ESI configuration to the capillary i.d. 83.

The curve 82 in FIG. 8 illustrates that an increase in sensitivity is achieved by the reduction in capillary i.d. 88. Experimental results have confirmed this down to a capillary i.d. 88 of 50 μm in size. Further increases in sensitivity are not generally expected after this point.

As illustrated by FIB. 8, the size of the capillary i.d. has only a small effect upon the current that reaches the detector 14. As noted above, the maximum stabilization is achieved when the value of electrospray current 34 approaches the value of the capillary current 32. The point 86 in FIG. 8 is a graphical representation. At this point, the current from the capillary 7 goes into the detector 14.

Analysis Procedure

The procedure utilizing the instant invention to analyze a sample is illustrated in FIG. 3 and is similar to the procedure using the apparatus illustrated in FIG. 2. Each process begins by placing the capillary 7 in a sample beaker 3 containing the sample solution 1, and applying voltage from a first high voltage source 5 via electrical lead 6 to the sample solution 1, thereby causing a portion of the sample solution 1 to flow into the capillary 7. When the desired sample volume is injected into the capillary 7, it is then placed into the beaker 4 containing a buffered solution 3. The constituents within the capillary 7 then move along the capillary 7, and through the ESI tip to the detector 14 via the ESI tip 13 where it is analyzed. When the apparatus is performing analysis of a sample solution 1 is analyzed, the constituents refer to the mixture of the sample solution 1 and the buffered solution 3. The velocity of the constituents within the capillary is dependent upon the combination of electrophoretic mobility of the individual analytes and the bulk electromotive flow of the fluid.

The type of detector 14 is not material to the invention; however, to date the best results have been obtained using mass spectrometry (MS), although ion mobility analyzers and other devices are alternative methods.

Test Results

Figure 9:
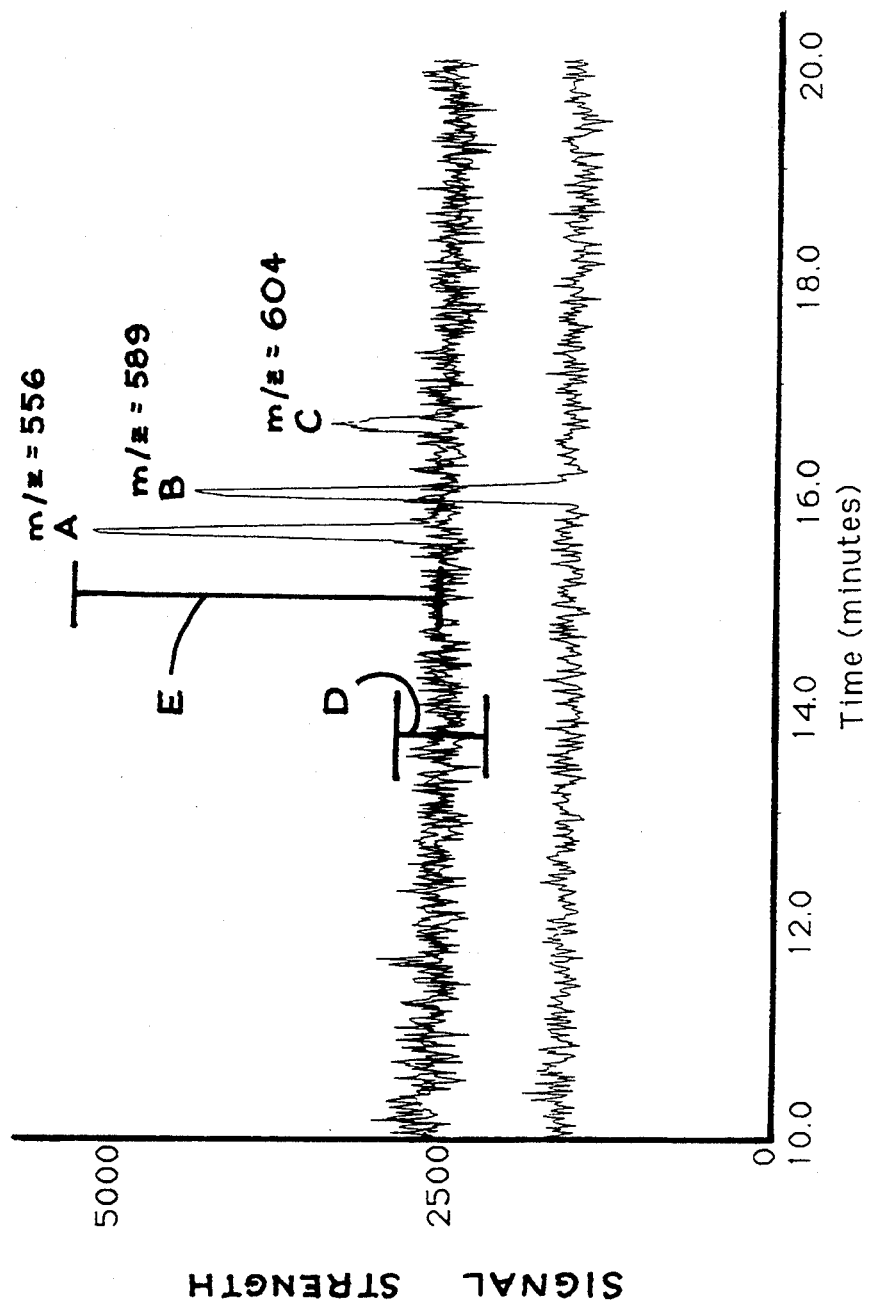
FIG. 9 is a graphical representation of the test results for a known sample illustrating the capabilities of the instant invention.

FIG. 9 shows the results achieved using the instant invention as a CZE-MS separation of two polypeptides where an injection of as little as 40 attomoles ($10^{-18}$ moles) is readily observable. An additional increase in sensitivity is expected as the quality control for the solvents and buffers is increased.

For this test, acetic acid was used as the buffer solution 3 (and the sheath liquid 36), and the MS was set for single ion monitoring (SIM). Commercially available samples of Leu-ENK (40 attomoles) and [Ala$^2$] Met-ENK (75 attomoles) were used.

Detection of the Leu-ENK is shown at peak A, and the [Ala$^2$] Met-ENK is shown at peak B, and impurity with an m/z value of 604 also appeared as peak C. ENK refers to enkephalin, MET refers to methionine, and Leu refers to leucine, a commercially available amino acid. An impurity with a m/z value of 604 also appeared during the test.

The sensitivity of the detection can be expressed in the signal to noise ratio (s/n). The strength of the signal of the detection of the particular constituent is expressed in the peak height, shown as amplitude B in FIG. 9, while the background noise height is shown as amplitude A in FIG. 9. The background noise D is that signal that is expressed by the detector 14 without a detection event being recorded.

The horizontal axis of FIG. 9 is marked in minutes. As mentioned earlier, the use of CZE causes a temporal distribution of the constituents in the capillary 7 that is dependent upon their electromorphetic mobility. This accounts for the distribution over time of the signals as expressed in FIG. 9.

Use with other Applications

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A system for conducting high resolution separation in a liquid composition for analysis of liquids by an analytical detector comprising:
   (a) a buffered solution;
   (b) a sample solution;
   (c) at least one source of sheath liquid; and
   (d) a means for electrospraying said sheath liquid, and said sample solution, in adjoining flows, wherein said means for electrospraying includes;
      (i) a first capillary, having a first capillary outlet with a metallic coating thereon, for the buffered solution and the sample solution, (ii) a first high voltage source for separating the components of a mixture of said buffered solution and said sample solution,
(iii) a second capillary having a capillary wall, for supply the sheath liquid in the adjoining flow about the first capillary,
(iv) a second high voltage source for providing electric potential across the sheath liquid, and
(v) a means for pumping said sheath liquid through said second capillary; and (e) an insulated nozzle for spraying said mixture, wherein the improvement comprises:

said second capillary wall electrically isolated between said second high voltage source and said insulated nozzle;

said means for electrospraying having said first high voltage source connected to said mixture; and said second high voltage source applied to the sheath liquid in said second capillary through said pumping means; and said first high voltage source and said second high voltage source creating a current through said first capillary, said current passing into said analytical detector;

whereby said current is stabilized.

2. The system in claim 1, wherein the first capillary outlet has a conical shape.

3. The system in claim 2, wherein the conical shaped outlet has a metallic coating.

4. A method for conducting high resolution separation in a liquid composition for analysis of liquids by an analytical detector comprising the steps of:
(a) providing a buffered solution,
(b) providing a sample solution,
(c) providing at least one source of sheath liquid, and
(d) electrospraying said sheath liquid, and said sample solution, in adjoining flows, wherein electrospraying includes;
  (i) providing a first capillary, having a first capillary outlet with a metallic coating thereon, for, the buffered solution and the sample solution,
  (ii) providing a first high voltage source for separating the components of a mixture of said buffered solution and said sample solution,
  (iii) providing a second capillary having a capillary wall, for supply the sheath liquid in the adjoining flow about the first capillary,
  (iv) providing a second high voltage source for providing electric potential across the sheath liquid, and
  (v) providing a means for pumping said sheath liquid through said second capillary; and
(e) spraying said mixture and sheath flow through an insulated nozzle, wherein the improvement comprises stabilizing a first capillary current and a first capillary flow by:
  (i) isolating said second capillary wall electrically from said second high voltage source and said insulated nozzle; and
  (ii) applying said first high voltage to said mixture;
  (iii) remotely applying said second high voltage source to the sheath liquid in said second capillary; and
  (iv) creating a current through said first capillary, said current passing into said analytical detector; whereby said current is stabilized.

5. The method in claim 4, further providing a conical shape on the first capillary outlet.

6. The method in claim 5, further providing a metallic coating on the conical shaped outlet.

* * * * *

UNITED STATES PATENT AND TRADEMARK OFFICE
CERTIFICATE OF CORRECTION

PATENT NO. : 5,423,964
DATED : 06/13/95
INVENTOR(S) : Smith et al.

It is certified that error appears in the above-indentified patent and that said Letters Patent is hereby corrected as shown below:

In column 4, line 64, after the word "solution" please insert --3--.

In column 5, line 31, please replace "30" with the number --41--.

In column 7, line 45, please replace "FIB." with --FIG.--.

Signed and Sealed this

Sixteenth Day of September, 1997

Attest:

BRUCE LEHMAN

Attesting Officer

Commissioner of Patents and Trademarks